(12) United States Patent
Winnacker et al.

(10) Patent No.: US 6,426,409 B1
(45) Date of Patent: Jul. 30, 2002

(54) NUCLEIC ACID MOLECULES THAT BIND PRION PROTEINS AND PROCESSES FOR THE PRODUCTION THEREOF

(76) Inventors: Ernst-Ludwig Winnacker, Dall'Armistrasse 41a, München D-80638; Stefan Weiss, Blutenstrasse 20, München D-80799; Michael Famulok, Schmaedelstrasse 28, München D-81245, all of (DE)

( * ) Notice: Subject to any disclaimer, the term of this patent is extended or adjusted under 35 U.S.C. 154(b) by 0 days.

(21) Appl. No.: 09/051,962

(22) PCT Filed: Oct. 25, 1996

(86) PCT No.: PCT/EP96/04671
§ 371 (c)(1),
(2), (4) Date: Oct. 2, 1998

(87) PCT Pub. No.: WO97/15685
PCT Pub. Date: May 1, 1997

(30) Foreign Application Priority Data

Oct. 26, 1995 (EP) ............................................. 95116890

(51) Int. Cl.$^7$ ............................................. C12N 15/11
(52) U.S. Cl. ................................... 536/23.1; 435/320.1
(58) Field of Search ............................... 514/44; 435/6, 435/320.1; 536/23.1

(56) References Cited

U.S. PATENT DOCUMENTS

| | | | |
|---|---|---|---|
| 4,917,998 A | * | 4/1990 | Burger et al. ................... 435/5 |
| 5,270,163 A | * | 12/1993 | Gold et al. ..................... 435/6 |
| 5,567,588 A | * | 10/1996 | Gold et al. ..................... 435/6 |

OTHER PUBLICATIONS

Lauhon et.al.; RNA aptamers that bind flavin and nicotinamide redox cofactors, 1995, J Am Chem Soc 117(4): 1246–1257.*
Huizenga et.al.; A DNA aptamer that binds adenosine and ATP, 1995, Biochemistry 34(2): 656–665.*
Harada et.al.; Molding a peptide into an RNA site by in vivo peptide evolution, 1997, Proc. Natl. Acad. Sci. vol. 94: 11887–11892.*
Kascsak et.al., The Role of Antibodies to PRP in the Diagnosis of Transmissible Spongiform Encephalopathies, 1993, Dev. Biol. Stand. 80: 141–151.*
Klug et al Mol Biol Reports 20: 97–107, especially see Fig. 1, p. 98, col. 1; p. 101, col. 1, lines 15–17, and paragraph 3 1994.*
Schreuder Veterinary Quarterly 15: 167–174, See especially: Table 1, p. 167; and the paragraph bridging pp. 167 and 168, Dec., 1993.*
Edenhofer et al J Virol 70: 4724–4728, See especially: abstract, lines 7–9, Jul., 1996.*
Weiss et al J Virol 69: 4776–4783, see abstract, and p. 4776, col. 2, lines 7–9, Aug., 1995.*
Kascsak et al Dev Biol Stand 80: 141–151, see especially: title and lines 15–17 of the abstract, 1993.*
Korth et al Nature 390: 74–77, see especially: lines 8–11 of abstract, Nov., 1997.*
Ausubel et al (In Current protocols in Molecular Biology, John Wiley and Sons, publishers, pp. 4.6.6, 4.6.7., 4.7.1, and 4.7.2, Mar., 1989.*
Macke et al. Accession No. W2834, May, 1996.*

* cited by examiner

*Primary Examiner*—James Ketter
*Assistant Examiner*—Richard Schnizer
(74) *Attorney, Agent, or Firm*—Roylance, Abrams, Berdo & Goodman, L.L.P.

(57) ABSTRACT

The invention describes a process for the identification and isolation of nucleic acid molecules capable of distinguishing the isoforms PrP$^c$ and PrP$^{Sc}$ of prion proteins as well as nucleic acid molecules obtainable by this process. Furthermore, pharmaceutical compositions and diagnostic compositions are described which comprise nucleic acid molecules specifically binding prion protein isoforms as well as diagnostic methods using such molecules.

4 Claims, 11 Drawing Sheets

A

I  CACUGCAGCAAUUCGUUGUGCGGGGAAUUUGAGGGACGAUGGGAAGUGGGACGAAUGACUCA
    UUGCCGCGGGUAGGGUUAGGCACC

II CACUGCAGCAAUGCGUUGUGUGGGAAUUUGAGGGACGAUGGGAAGUGGGACGAAUGACUC
    AUUGCCGCGGGUAGGGUUAGGCACC

B

III CACUGCUACCUUAGAGAGUAGGAGCGGGGACGAGGGGGUUGUUGGGUAUGAUCCAUAC
     AUUAGGAAGCUGGUGAGCUGGCACC

IV  CACUGCUACCUUAGAGAGUAGGAGCGGGGACGAGGGGGUUGUUGGGUAUGAUCCAUAC
     AUUAGGAAGCUGGUGAGCUGGCACC

V   CACUGCUACCUUAGAGAGUAGGAGCGGGGACGAGGGGGUUGUUGGGUAUGAUCCAUAC
     AUUAGGAAGCUGGUGAGCUGGCACC

C

VI   CACUGCGACAUGGGGAAGAGGGGAAGAGGGUUGUCGGGAGAUAAUGUCGCGAAACUAAGAACU
      CUAAGAGCUGCCCGUGGCACC

VII  CACUGCGACAUGGGGAGGAGGGGAAGAGGGUUGUCGGGAGAUAAUGUCGCGAAACUAAGAAC
      UCUAAGAGCUGCCGUGGCACC

VIII CACUGCGACAUGGGGAAGAGGGGAAGAGGGUUGUCGGGAGAUAAUGUCGCAAAGCUAAGAAC
      UCUAAGAGCUGCCGUGGCACC

IX CACUGCUUGCUCGUUGCACUGUGAUAUG*UGGG*UUUAGGAUAGGG*AAGA*GGG*AAGA*GAAUAUCCGUCU
GAACGAGGGCACC

X CACUGCUGCUAUUCAGU*GGG*UUGU*GGG*AGAAGGG*U*AGG*GGG*AUGAUGAAAGCAGCUCGUGUGAUUCUUUCUGAA
GACCGGCACC

XI CACUGCCGCUCAUAU*GGG*CCACAUCUCAAAGU*GGG*AAUGUGGG*GAU*GGG*AAGAGGG*AUGAUUAAGAUGGCCACAUA
UUCGGCACC

XII CACUGCGAGGAUGC*GGG*ACGAGGG*AACGAGGG*AACGA*GGG*AUGAAUCCUUGUAGUGAGAUAGCUUCCCCAACAUG
UCCAGGCACC

XIII CACUGCUUGCGUCAUUGGCAAGA*GGG*GAUGCGGG*AAAGAUU*GGG***AACACCGCACCAAUAAUGUGAGUGU
GAGGGCACC

E

XIV CACUGCCCUCGAAAACUGUGAAGAGUACGCUUUAACUGUCCGUGUG*GAUU*GACCAUAGACCCGUCCCUGG
ACAGGCACC

Fig. 5B

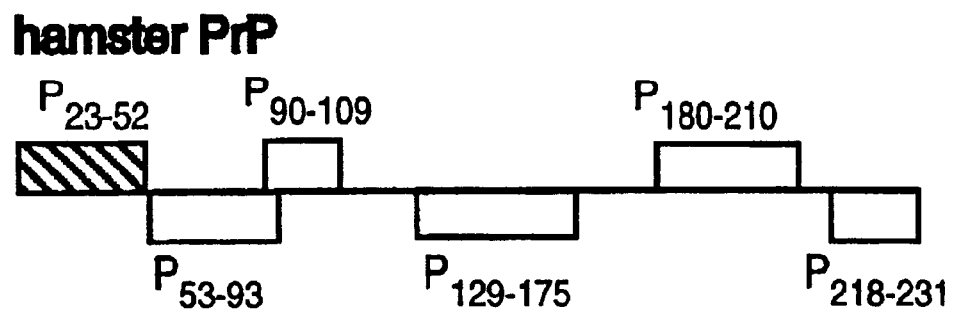
Fig. 7A   Aptamer Motif I
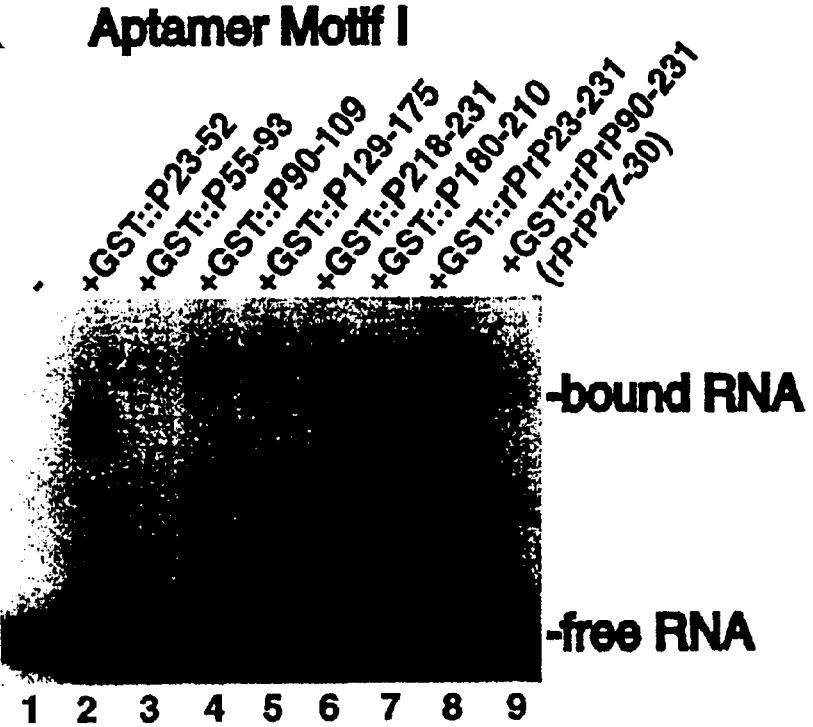
Fig. 7B   Aptamer Motif II
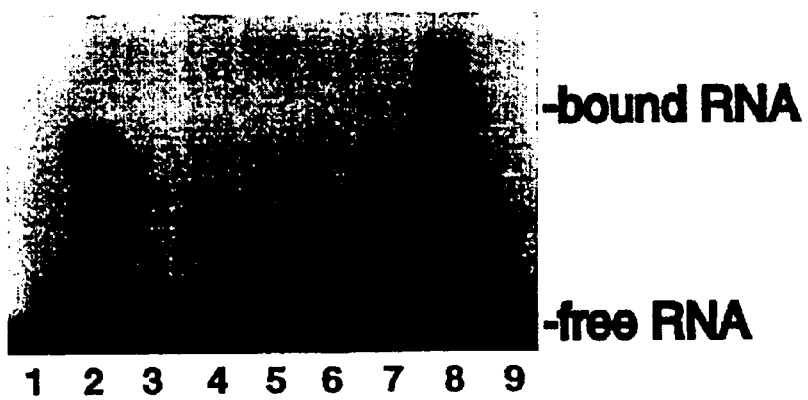

NUCLEIC ACID MOLECULES THAT BIND PRION PROTEINS AND PROCESSES FOR THE PRODUCTION THEREOF

BACKGROUND OF THE INVENTION

The present invention relates to a process for the identification and isolation of nucleic acid molecules capable of distinguishing the isoforms $PrP^c$ and $PrP^{Sc}$ of prion proteins as well as to the nucleic acid molecules obtainable by this process. Furthermore, the invention relates to pharmaceutical and diagnostic compositions comprising said nucleic acid molecules.

Proteinaceous infectious particles called prions are thought to be the causative agent of transmissible spongiform encephalopathies (TSEs) such as Scrapie of sheep, bovine spongiform encephalopathy (BSE) of calf, transmissible minc encephalopathy (TME) of mink as well as Kuru, Gerstmann-Sträussler-Scheinker syndrome (GSS), Creutzfeldt-Jakob-Disease (CJD) and fatal familial insomnia (FFI) in the case of humans (Prusiner, 1982). The main component of prions associated in amyloid-like rods (Prusiner et al., 1983; 1984) or scrapie associated fibrils (SAF; Hope et al., 1986) was found to be the prion protein PrP27-30 (Prusiner et al., 1981; Prusiner et al., 1983), an N-terminal truncated, highly protease resistant version of the prion protein $PrP^{Sc}$ (Oesch et al., 1994), which is also found to a minor extend in prion preparations (Prusiner et al. 1983). PrP27-30, which is devoid of 67 amino acids at the aminoterminal end, results from $PrP^{Sc}$ by proteinase K digestions (Prusiner et al., 1984; Stahl et al., 1993) or by lysosomal protease digestion (Caughey et al., 1991). The distribution of $PrP^{Sc}$ and PrP27-30 in prion preparations varies dependent from the absence or presence of proteases.

No specific nucleic acid could be detected so far in prion preparations (Kellings et al., 1992) suggesting that the prion is infectious and can replicate in the absence of any nucleic acid (Prusiner, 1982). According to the protein-only hypothesis (Prusiner, 1982) exogenous $PrP^{Sc}$/PrP27-30 could convert the ubiquitous cellular isoform $PrP^c$ to $PrP^{Sc}$/PrP27-30. It is assumed that chaperons may be involved in this process (Edenhofer et al., 1996). $PrP^{Sc}$/PrP27-30 could appear as a monomer (Prusiner. 1982) or as a nucleation or crystal seed consisting of a $PrP^{Sc}$/PrP27-30 oligomer (Lansbury and Caughey. 1995). $PrP^c$ differs from PrP27-30 only with respect to its secondary structure: the $\alpha$-helical and $\beta$-sheet contents of $PrP^c$ are 42% and 3%, respectively (Pan et al., 1993). In contrast. the $\alpha$-helical and $\beta$-sheet contents of PrP27-30 were proven to be 21% and 54%. respectively (Pan et al., 1993). These results indicate that the conversion of $PrP^c$ to $PrP^{Sc}$/PrP27-30 is most likely concomitant with extreme alterations in the secondary structure of the prion protein. Although a series of experiments employing knockout mice which no longer express $PrP^c$ suggest that cellular prion proteins could play a crucial role in a number of cellular processes (Collinge et al., 1994; Sakaguchi et al., 1996: Tobler et al., 1996), a precise physiological role of $PrP^c$ remains speculative. It is, however, proven that $PrP^c$ is necessary for the development of transmissible spongiform encephalopathies (Büeler et al., 1993; Brandner et al., 1996).

Translation of the mRNA from Scrapie infected Syrian golden hamster has led to a 254 amino acid protein including a 22 amino acid signal peptide at the $NH_2$-terminus and a 23 amino acid signal sequence at the carboxy terminus (Oesch et al., 1985; Basler et al., 1986). The mature protein $PrP^c$ as well as the Scrapie isoform $PrP^{Sc}$ contain amino acids 23 to 231. Only $PrP^{Sc}$ can be processed to the proteinase K resistant isoform PrP27-30 (amino acids 90–231) consisting of 142 amino acids (Prusiner et al, 1984).

This property has been used to design a diagnostic assay for diseases in connection with prion proteins in which a probe is treated with proteinase K in order to degrade all $PrP^c$ and then reacted with an antibody directed against prion proteins (Groschup et al., 1994). However, this assay has the disadvantage that sensitivity might be hampered by the fact that the proteinase K digestion of $PrP^c$ is not complete, thereby leading to false positive results. Furthermore, the additional step of proteinase K digestion is time consuming. In order to be able to directly assay for the presence or absence of $PrP^c$ and/or $PrP^{Sc}$ one would need antibodies which could distinguish between these two isoforms.

However, so far attempts to provide antibodies that can distinguish between the cellular isoform $PrP^c$ and the isoforms $PrP^{Sc}$, as well as the truncated version PrP27-30, have failed (Groschup et al.. 1994 and ref. therein). Thus, up to now it was not possible to distinguish the isoforms $PrP^c$ and $PrP^{Sc}$ of prion proteins by immunological or other means which would be the prerequisite for a simple and reliable method of diagnosing a transmissible spongiform encephalopathy.

Therefore, the technical problem underlying the present invention is to provide a process for the identification and isolation of molecules which are capable of distinguishing between the isoforms $PrP^c$ and $PrP^{Sc}$ or PrP27-30 of prion proteins and which are useful tools for diagnosis and therapy of transmissible spongiform encephalopathies.

The solution to said technical problem is achieved by the provision of the embodiments characterized by the patent claims.

SUMMARY OF THE INVENTION

Thus, the present invention relates to a process for the identification and isolation of nucleic acid molecules which are capable of distinguishing between the isoforms $PrP^c$ and $PrP^{Sc}$ or PrP27-30 of prion proteins associated with transmissible spongiform encephalopathies comprising the steps of (i) incubating a prion protein isoform or peptide fragment or derivative of this prion protein isoform with a pool of nucleic acid molecules comprising different sequences;

(ii) selecting and isolating those nucleic acid molecules which are capable of binding to said prion protein isoform or fragment or derivative thereof;

(iii) optionally, amplifying the isolated nucleic acid molecules and repeating steps (i) and (ii); and (iv) determining the binding specificity of the isolated nucleic acid molecules for the $PrP^c$ and $PrP^{Sc}$ or PrP27-30 isoforms of prion proteins.

DETAILED DESCRIPTION OF THE INVENTION

The process according to the invention is based on a method called "in vitro selection". This method allows for the identification of nucleic acid molecules (RNA, modified RNA. ssDNA or dsDNA) which bind with high affinity to a defined molecular target from a large randomized population of nucleic acid molecules (Tuerk and Gold, 1990; Famulok and Szostak, 1992). Using this method it has been possible to isolate nucleic acids specifically recognizing a variety of protein targets including HIV-1 reverse transcriptase (Tuerk et al., 1992), HIV-1 Integrase (Allen et al., 1995), human α-thrombin (Kubik et al., 1994) and Drosphila sex-lethal protein (Sakashita and Sakamoto, 1994). However, up to now it has not been possible to provide by this method nucleic acid molecules being capable of distinguishing the two isoforms of prion proteins, $PrP^c$ and $PrP^{Sc}$. In the scope of the present invention the term $PrP^c$ comprises the cellular isoform of the prion protein as well as fragments and derivatives thereof irrespective of the source organism. The term $PrP^{Sc}$ comprises the isoform of the prion protein associated with various transmissible spongiform encephalopathies. This term also comprises fragments of this prion protein isoform such as the truncated version of the isoform $PrP^{Sc}$, the prion protein PrP27-30, which is the main component of prions. In particular, this term also includes $PrP^{Sc}$ proteins of the various Scrapie strains including those adapted to hamster, mouse or other vertebrates. Also included are derivatives of the prion protein isoform $PrP^{Sc}$.

The term derivatives includes chemically modified versions of the prion protein isoforms $PrP^c$ and $PrP^{Sc}$ as well as mutants of these proteins, namely proteins which differ from the naturally occurring prion protein isoforms at one or more positions in the amino acid sequence, as well as proteins that show deletions or insertions in comparison to the naturally occurring prion protein isoforms. Such mutants can be produced by recombinant DNA technology or can be naturally occurring mutants. The term derivatives also embraces proteins which contain modified amino acids or which are modified by glycosylation, phosphorylation and the like.

According to the invention it is possible to use as nucleic acid molecules single or double stranded nucleic acid molecules, such as RNA, modified RNA, single stranded DNA or double stranded DNA.

A pool of nucleic acid molecules, which constitutes the starting material from which nucleic acid molecules are selected which specifically bind to one of the isoforms of the prion protein is defined as a mixture of nucleic acid molecules of different sequences. This pool can be any mixture of nucleic acid molecules, preferably a pool of randomized molecules. Preferably the nucleic acid molecules of the pool are chemically synthesized or produced by in vitro transcription.

In the case of RNA molecules the RNA pool which is screened for molecules specifically binding to one of the isoforms of a prion protein is preferably the RNA pool M111.1 described in Famulok (1994). This pool consists of RNA molecules of 111 nucleotides randomized at 74 positions and results from the transcription of corresponding DNA sequences. The pool M111.1 contains RNA molecules with approximately $1 \times 10^{15}$ different sequences.

The process according to the invention can be used to identify and isolate nucleic acid molecules which can distinguish between the two isoforms of prion proteins, $PrP^c$ and $PrP^{Sc}$, associated with a transmissible spongiform encephalopathy such as Scrapie of sheep, bovine spongiform encephalopathy (BSE) of calf, transmissible mink encephalopathy (TME) of mink, Kuru, Gerstmann-Sträussler-Scheinker Syndrome (GSS), fatal familial insomnia (FFI), Creutzfeldt-Jakob Disease (CJD) in the case of humans, chronic wasting disease (CWD) of mule, deer and elk or feline spongiform encephalopathy (FSE) of cats. Transmissible spongiform encephalopathies are also known from nyala, gemsbok, arabian oryx, greater kudu, eland, ankole, moufflon, puma, cheetah, scimitar horned oryx, ocelot and tiger.

The step of incubating the pool of nucleic acid molecules with a prion protein can be carried out in different ways. In one preferred embodiment of the invention the protein is immobilized, for example, on a matrix such as a gel or a resin for chromatography. The immobilization can be achieved by means known to the person skilled in the art. For example, the protein can be covalently linked to a matrix or can be bound to it by a specific interaction between a group present on the matrix and a domain of the protein specifically recognizing this group. Such a domain can be fused to a prion protein by recombinant DNA technology as will be discussed below.

If the prion protein is immobilized nucleic acid molecules which do not bind to the prion protein can be removed after incubation by washing with an appropriate buffer Subsequently the nucleic acid molecules binding to the prion protein can be eluted from the immobilized protein, for example by 8M urea, and further purified, for example, by phenol extraction and precipitation.

In another preferred embodiment the prion protein is in solution. In this case the nucleic acid molecules binding to the prion protein can be isolated, for example, by carrying out a gel retardation assay and isolating the protein/nucleic acid complex. Subsequently the nucleic acid molecules can be isolated from the complex and further purified by known methods.

According to the invention it is possible to amplify the nucleic acid molecules obtained by steps (i) and (ii), for example by in vitro transcription, reverse transcription or polymerase chain reaction or a combination of these techniques, and to repeat steps (i) and (ii). This leads to a further selection and amplification of nucleic acid molecules which bind specifically to the used prion protein. If several cycles of steps (i) to (iii) of the process are performed, it is possible to use in one or more cycles an immobilized protein and in one or more cycles a protein in solution. A cycle in which a protein in solution is used permits the elimination of nucleic acid molecules binding to the matrix on which the immobilized protein is fixed.

The prion protein used in the process can be any of the known prion protein isoforms or a fragment or derivative of such a protein.

In a preferred embodiment the prion protein is the isoform $PrP^{Sc}$ present in the prion. In a specifically preferred embodiment the N-terminally truncated version of $PrPS^{Sc}$, PrP27-30, is used. In this context $PrP^{Sc}$ and PrP 27-30 refer to any of these isoforms which can be found in an organism affected with a transmissible spongiform encephalopathy.

In a further preferred embodiment the prion protein used in the process is the cellular isoform $PrP^c$, most preferably the processed form $PrP^c$23-231 which comprises amino acids 23 to 231 of $PrP^c$.

In another preferred embodiment the prion protein used in the process is a recombinant protein. This means that the protein is produced by recombinant DNA technology, namely by expression from a cloned DNA sequence.

More preferably, the prion protein is part of a fusion protein. Such a fusion protein can comprise beside the prion protein a protein or protein domain which confers to the fusion protein a specific binding capacity. For example, such a domain may be an oligohistidine (Le-Grice et al., 1990), Calmoduline binding peptide (CBP) (Carr et al., 1991), S-peptide (ribonuclease A) (Kim and Raines, 1993), FLAG (Kawase et al., 1995), green-fluorescent protein (GFP) (Hampton et al., 1996), BTag (Wang et al., 1996), or maltose-binding protein (MBP) (Aitken et al., 1994, Richards and Wyckoff, 1971). Proteins comprising such a domain can be immobilized for example, on IMAC-$Ni^{2+}$, Calmodulin, S-protein 104 aa (Kim and Raines, 1993), anti-FLAG-antibodies, anti-GFP-antibodies, BTag-antibodies or maltose. Elution can then be achieved by a method well-known in the art. In a preferred embodiment the prion protein is fused to glutathione-S-transferase. Such a fusion protein possesses a high affinity for glutathione and can thus be immobilized on a matrix comprising glutathione, such as glutathione-sepharose.

In the last step of the process according to the invention the isolated nucleic acid molecules are tested for their binding to the different isoforms, $PrP^c$ and $PrP^{Sc}$, of a prion protein. Those nucleic acid molecules are selected which specifically bind to only one of the isoforms.

Thus, the process according to the invention allows the identification and isolation of nucleic acid molecules which specifically bind to one of the isoforms of a prion protein or a fragment or derivative thereof and thereby allow the distinguishing of the different isoforms. These nucleic acid molecules therefore show an unexpected high specificity, which is even higher than the specificity of poly- or monoclonal antibodies which cannot distinguish between the isoforms of prion proteins. The process of the invention has been successfully carried out to isolate RNA molecules which can distinguish between the isoforms $PrP^c23-231$ and PrP27-30 from Syrian Golden Hamster. In this case the isoforms were recombinant proteins fused to glutathicne-s-transferase (GST::$PrP^c23-231$ and GST::rPrP27-30). The recombinant rPrP27-30 protein is identical in sequence to the natural PrP27-30 protein but reveals in contrast to the natural isoform proteinase K sensitivity.

Furthermore, the present invention relates to nucleic acid molecules obtainable by a process according to the invention, namely to RNA, single stranded DNA or double stranded DNA molecules which bind to one of the isoforms of a prion protein. These include nucleic acid molecules which specifically bind to the cellular isoform $PrP^c$, namely to the processed form $PrP^c23-231$, or specifically to the isoform $PrP^{Sc}$, namely to the truncated version PrP27-30, or specifically to derivatives of these proteins.

In a preferred embodiment the nucleic acid molecules of the invention comprise four stretches of three consecutive guanosine residues separated by single stranded regions between four and seven nucleotides long. More preferably, the nucleic acid molecules comprise a nucleotide sequence as depicted in SEQ ID NO: 15, SEQ ID NO: 16 or SEQ ID NO: 17.

In another preferred embodiment, the region comprising the four guanosine stretches is flanked by two variable regions of predominantly Watson-Crick covariation. In particular, the nucleic acid molecules preferably comprise a nucleotide sequence as depicted in any one of SEQ ID NO: 1 to 13 and more preferably a nucleotide sequence as depicted in SEQ ID NO: 18.

In a preferred embodiment the nucleic acid molecules according to the invention are further modified at one or more positions in order to increase their stability and/or to alter their biochemical and/or biophysical properties.

The present invention also relates to pharmaceutical compositions comprising nucleic acid molecules according to the invention. Such compositions can optionally comprise pharmaceutically acceptable carriers.

These compositions may be useful for the therapy of transmissible spongiform encephalopathies such as those listed above. It may be possible, for example, to suppress the conversion of the isoform $PrP^c$ into the prion associated isoform $PrP^{Sc}$ by applying nucleic acid molecules which specifically bind to $PrP^c$.

Furthermore, the present invention relates to diagnostic compositions comprising nucleic acid molecules according to the invention. Such compositions may contain additives commonly used for diagnostic purposes. The nucleic acid molecules and the diagnostic compositions according to the invention can be used in methods for the diagnosis of transmissible spongiform encephalopathies. Such a method comprises, for example, the incubation of a sample taken from a body with at least one kind of nucleic acid molecules according to the invention and the subsequent determination of the interaction of the nucleic acid molecules with the isoforms $PrP^c$ and $PrP^{Sc}$ of a prion protein.

Since during the occurrence of a transmissible spongiform encephalopathy the amount of the isoform $PrP^{Sc}$ increases and the total amount of the cellular isoform $PrP^c$ decreases, it is in principle possible to use for diagnosis nucleic acid molecules which bind to one or the other of the two isoforms.

On the one hand, it is possible to use at least one kind of nucleic acid molecule according to the invention in order to quantitatively determine the amount of at least one isoform of a prion protein in a sample.

On the other hand, it is possible to use nucleic acid molecules which specifically bind the $PrP^c$ isoform in combination with nucleic acid molecules which specifically bind the $PrP^{Sc}$ isoform in order to determine the absolute and/or relative amount of the isoforms in a sample.

In a preferred embodiment the sample may be obtained from various organs, perferably from tissue, for example, from brain, tonsils, ileum, cortex, dura mater, Purkinje cells, lymphnodes, nerve cells, spleen, muscle cells, placenta, pancreas, eyes, backbone marrow or peyer'sche plaques, for example in the form of thin sections. Alternatively the sample may be obtained from a body fluid, preferably from blood, cerebrospinal fluid, milk or semen.

In the case that brain is used as a sample, diagnosis is in most cases performed post mortem. Exceptionally, brain biopsies can be performed on the alive organism. The brain can originate from any organism that might be afflicted with a transmissible spongiform encephalopathy, such as sheep, calf, mice, cats, hamster, mule, deer, elk or humans or from other organisms which may be afflicted by a TSE as mentioned above. The brain should originate from organisms which are $PrP^{0/0}$ (knock-out), $PrP^{Sc}$ (infected) and $PrP^c$ (wild-type) or of unknown PrP-status.

In the case that blood, milk, cerebrospinal fluid, semen or tissue from other organs as mentioned above is used as a sample, diagnosis is possible for living individuals.

Furthermore, the nucleic acid molecules according to the invention can be used to identify three dimensional structures which are necessary for the specific binding of a prion protein isoform. With the help of this information other chemical compounds can be isolated or synthesized which can specifically bind prion protein isoforms. Thus, the present invention also relates to chemical compounds other than nucleic acid molecules which are based on the information derived from a three dimensional structure of a nucleic acid molecule according to the invention, selected from the group consisting of inorganic or organic compounds, preferably sugars, amino acids, proteins or carbohydrates.

In the following, (r)PrP$^c$ stands for rPrP23-231. Furthermore, rPrP27-30 stands for rPrP90-231 (Syrian Golden Hamster).

Figure 1:
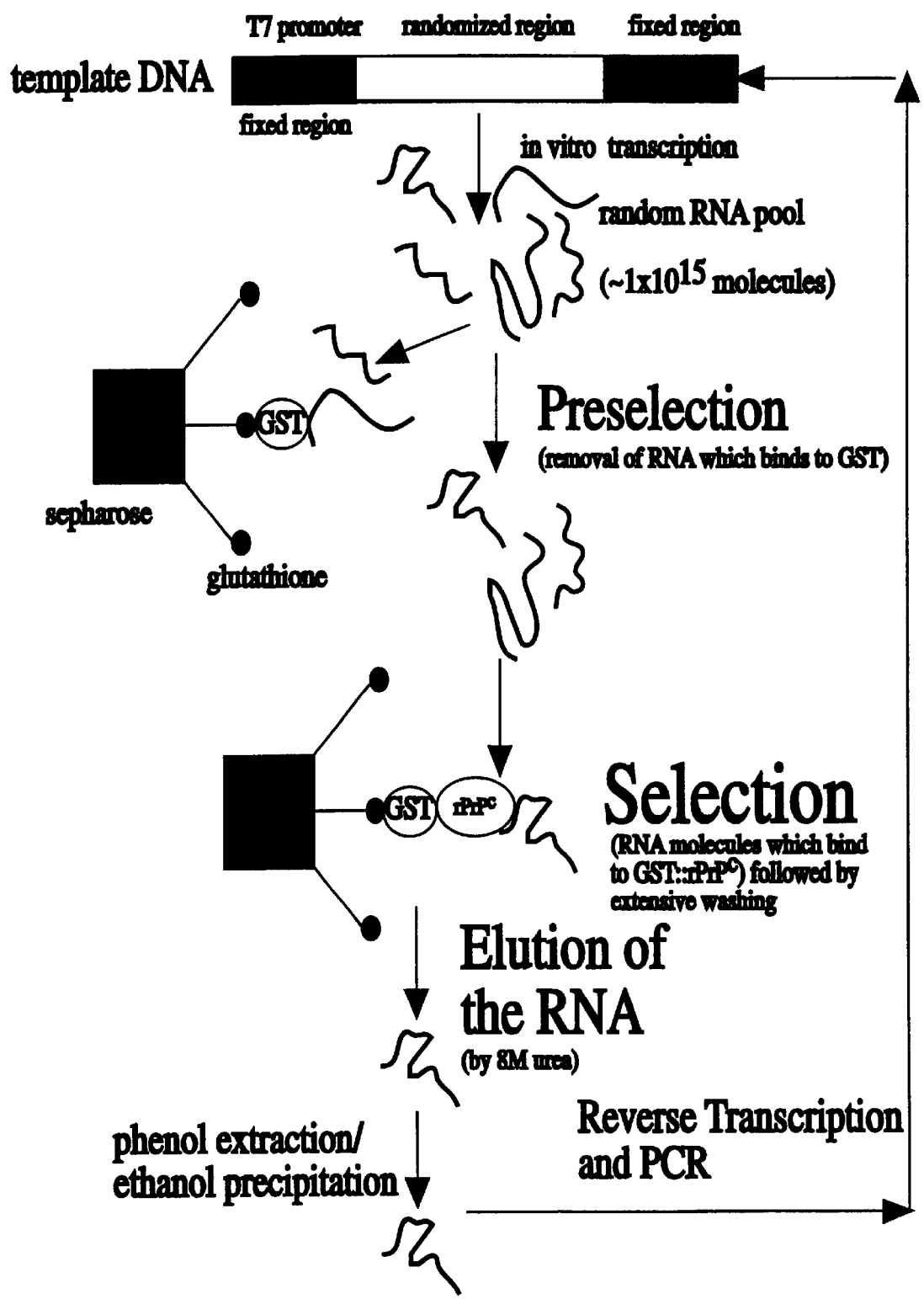
FIG. 1A: Illustrates schematically the method for in vitro selection of RNA molecules specifically binding to the immobilized fusion protein GST::r$PrP^c$ (GST:: rPrP23-231) (GST=glutathione-S-transferase; PCR=Polymerase chain reaction).
Figure 1:
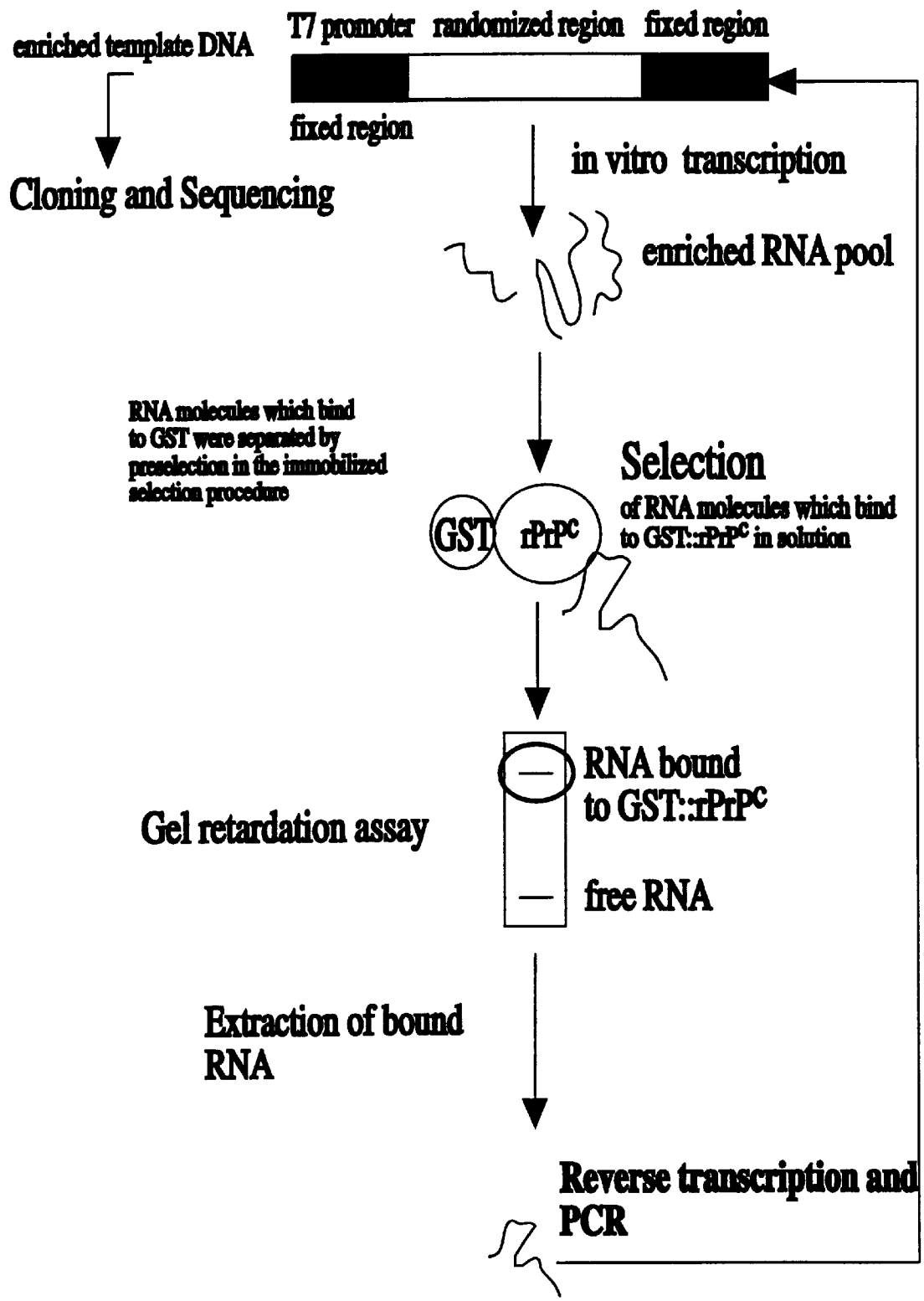

FIG. 1B: Illustrates schematically a further step in the in vitro selection of RNA molecules specifically binding to GST::rPrP$^c$ using GST::rPrP$^c$ in solution and a gel retardation assay.

Figure 2:
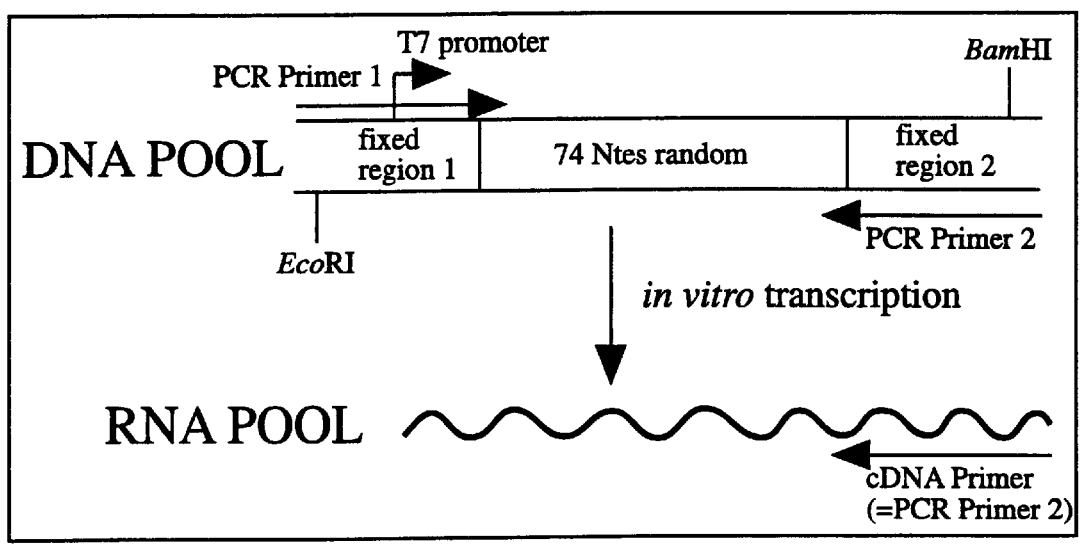

FIG. 2: Schematically illustrates the construction by in vitro transcription of the randomized RNA pool M111.1 (Famulok, 1994) (Ntes=nucleotides).

Figure 3:
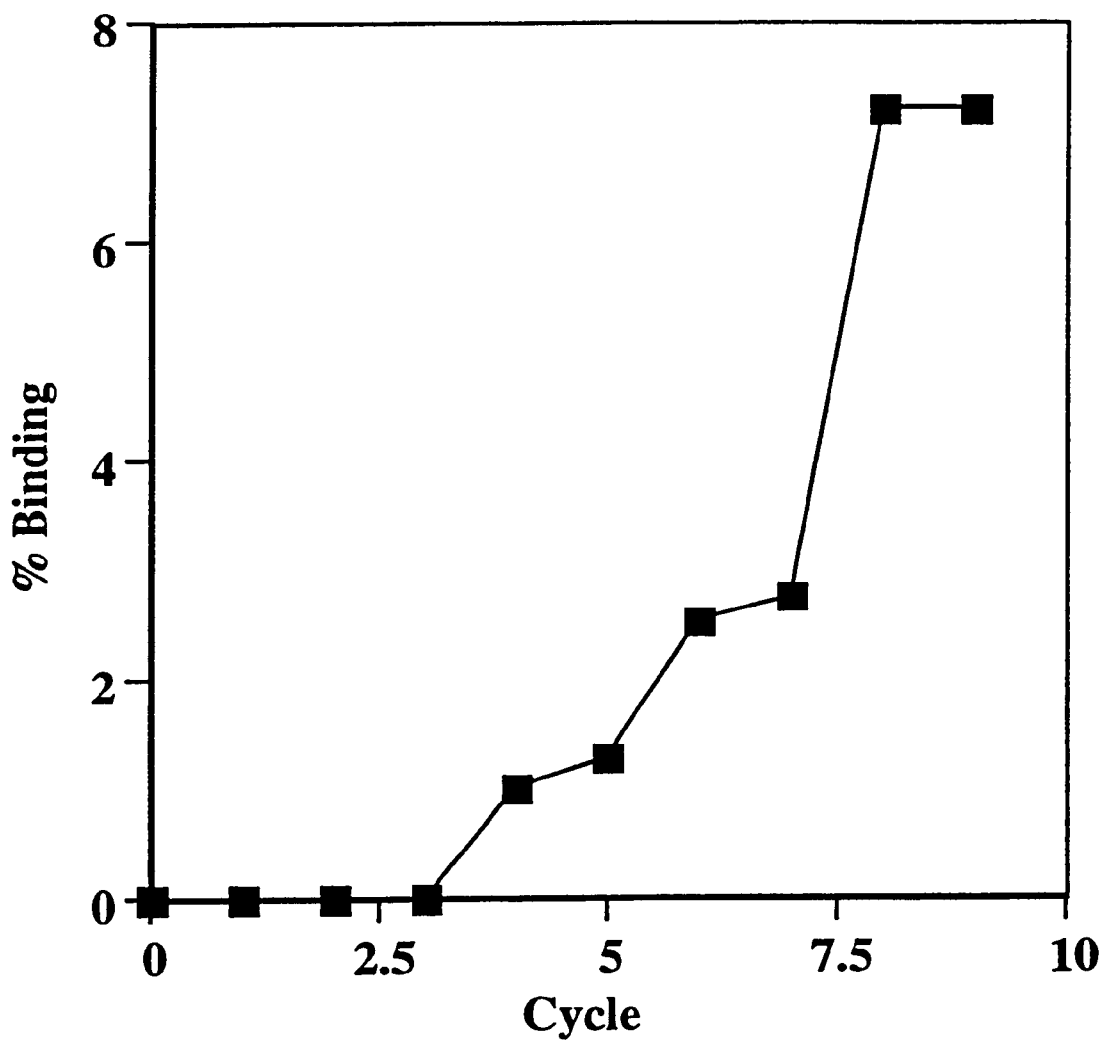

FIG. 3: Shows the percentage of RNA binding to immobilized GST::rPrP$^c$23-231 after each cycle of the process described in Example 1.

Radioactivity associated with GST::rPrP$^c$ beads after removal of the supernatant was set to 100%. Radioactivity retained after 4 washing steps represents the percentage of RNA binding.

FIG. 4A: Shows the binding of selected RNAs and unselected RNAs to GST, GST::rPrP$^c$ and GST:rPrP27-30. 5' labeled RNA was incubated in the presence of the proteins, filtered over BA85 nitrocellulose on a millipore slot blot apparatus. Retained radioactivity was quantified by Cerenkov counting.

FIG. 4B: Shows that the in vitro selected RNA molecules of Example 1 distinguish between PrP$^c$ and rPrP27-30 from the Syrian Golden Hamster. Gel a: 5' labeled RNA molecules after 9 cycles were incubated in the presence of GST, GST::PrP$^c$ and GST::rPrP27-30, and analyzed on 0.7% non-denaturing agarose gels. Gels were fixed by 5% TCA, dried and subjected to autoradiography. The GST::rPrP$^c$/RNA complex from the 9th cycle was excised from the gel, the RNA extracted, reverse transcribed, PCR amplified and in vitro transcribed (see FIG. 1B). This procedure was repeated twice for cycle 10 and 11. Gel b: The 5' labeled RNA—after 11 cycles—was again incubated in the presence of GST, GST::rPrP$^c$ and GST::rPrP27-30 and analyzed as described above.

FIG. 5: Sequences of selected RNA aptamers directed against rPrP$^c$23-231 fused to GST from hamster by in vitro selection. The aptamers belong to several groups of molecules. RNA aptamers of group (A) (motif I) and (B) (motif II) can harbor G-quartet motifs and distinguish between rPrP23-231 (rPrP$^c$) and rPrP90-231 (rPrP27-30). RNA aptamers of group (C) (motif III) could also have G-quartet motifs but interact with rPrP23-231 (rPrP$^c$) and rPrP90-231 (rPrP27-30). (D) Aptamers with unique G-quartets (5 out of 6 aptamers shown). Aptamers of group (E) lack any G-quartet motif and bind to GST (one out of 6 aptamers shown). Sequences I to XIV correspond to SEQ ID NOS: 1 to 14.

Figure 6:
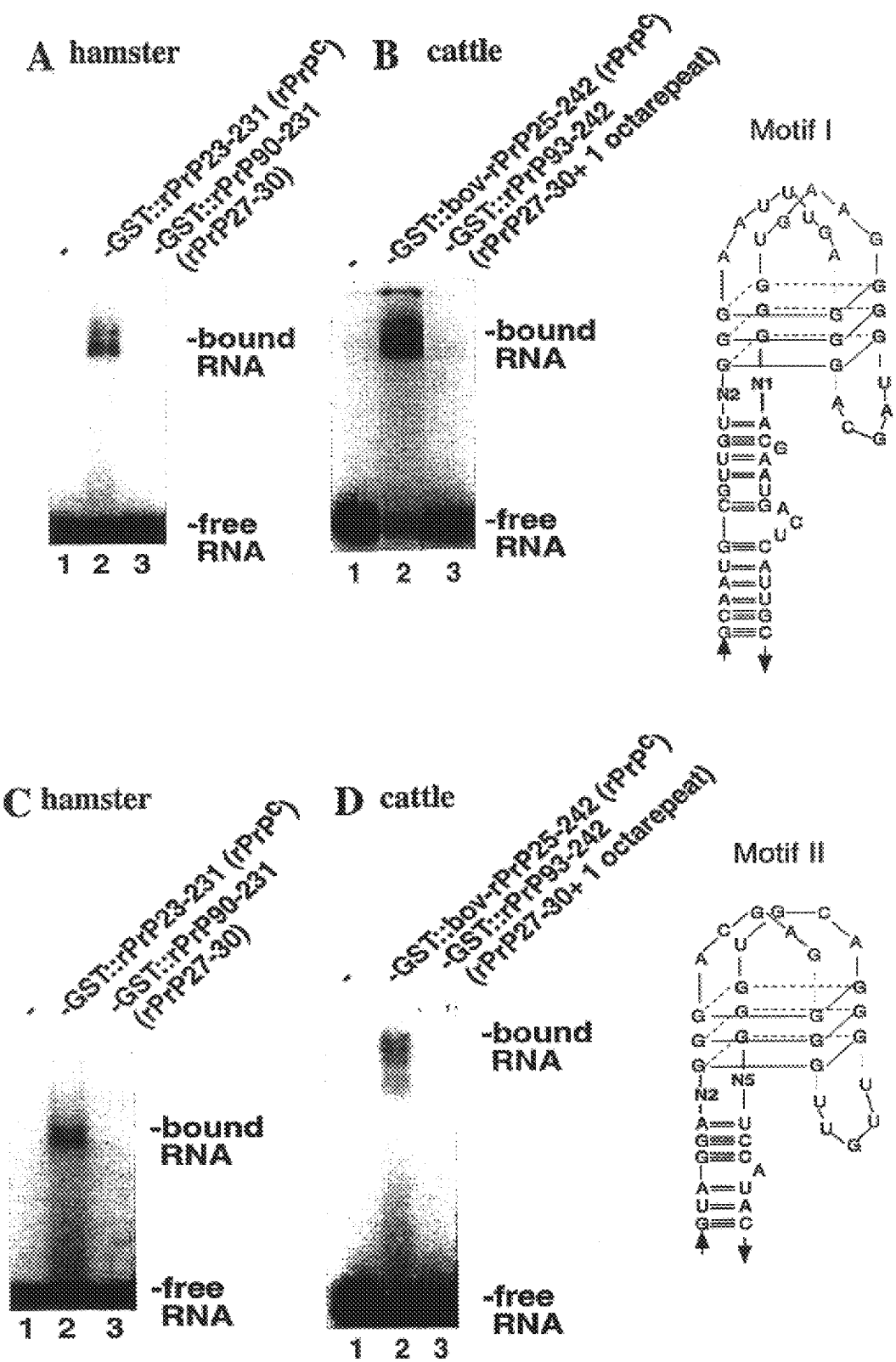

FIG. 6: RNA aptamers motif I and II distinguish the recombinant prion protein isoforms rPrP23-231 (rPrP$^c$) and rPrP90-231 (rPrP27-30) from hamster and calf. (A) 4 pMols of labeled RNA Ap1 (motif I; lanes 1–3) were incubated in the presence of 40 pMols each of recombinant GST::rPrP23-231 (rPrP$^c$) (lane 2) and GST::rPrP90-231 (rPrP27-30) from Syrian golden hamster (lane 3). (B) 4 pMols of labeled RNA Ap1 (motif I; lanes 1–3) were incubated in the presence of 40 pMols each of recombinant GST::bov-rPrP25-242 (rPrP$^c$) (lane 2) and GST::bov-rPrP93-242 (rPrP27-30+1 octarepeat) from calf (lane 3).(C) 4 pMol of labeled RNA motif II (lanes 1–3) were incubated in the presence of GST::rPrP23-231 (rPrP$^c$) (lane 2) and GST::rPrP90-231 (rPrP27-30) (lane 3) from hamster. Reaction assays were analyzed on 0.7% agarose gels. (D) 4 pMols of labeled RNA Ap2 (motif II; lanes 1–3) were incubated in the presence of 40 pMols each of recombinant GST::bov-rPrP25-242 (rPrP$^c$) (lane 2) and GST::bov-rPrP93-242 (rPrP27-30+1 octarepeat) from calf (lane 3). The additional bovine octarepeat extends from aa 93 to 101.

FIG. 7: Mapping of the RNA aptamer—PrP interaction site of hamster and calf. (A) 4 pMols of labeled RNA aptamer motif I (lanes 1–9) and (B) 4 pMols of labelled RNA aptamer motif II (lanes 1–9) were incubated in the presence of 40 pMol each of GST::rPrP23-231 (rPrP$^c$) (lanes 8), GST::rPrP90-231 (rPrP27-30) (lanes 9) from hamster and 20 pMol each of GST::P23-52 (lanes 2), GST::P55-93 (lanes 3), GST::P$_{90-109}$ (lanes 4). GST::P$_{129-175}$ (lanes 5), GST::P$_{218-231}$ (lanes 6) and GST::P$_{180-210}$ (lanes 7). Reaction assays were analyzed on 0.7% agarose gels. (Top) Schematic presentation of the hamster PrP region. Hatched box, PrP region interacting with the aptamers. Void boxes, PrP region not interacting with the aptamers. (C) 4 pMols of labelled RNA aptamer motif II (lanes 1–4) were incubated in the presence of 40 pMol each of bovine GST::bovP$_{25-92}$ (lane 2), GST::bovP$_{93-120}$ (lane 3) and 20 pMol each of bovine GST::bov-rPrP93-242 (rPrP27-30+1 octarepeat; lane 1) and hamster GST::P23-89 (lane 4).

The Examples illustrate the invention.

EXAMPLE 1

In vitro Selection of RNA Molecules Specifically Binding GST::rPrP$^c$23-231

An in vitro selection procedure (schematically outlined in FIGS. 1A and B) was carried out using recombinant PrP23-231 (rPrP$^c$) from the Syrian Golden Hamster fused to GST (Weiss et al., 1995) and RNA pool M 111.1 (Famulok, 1994).

Cycles 1–9: 5'[γ-$^{32}$P]-ATP labeled (1.Cycle) or [α-$^{32}$P]-UTP labeled (Cycles 2–10) RNA M111.1 (Famulok, 1994) (6,8 nMol (first), 1.82 nMol (2nd), 914 pMol (3rd), 665 pMol (4th), 2.07 nMol (5th), 831 pMol (6th), 2.7 nMol (7th), 1.94 nMol (8th and 9th cycle was incubated in the presence of immobilized GST (185 pMol) synthesized in the Baculovirus system (Weiss et al., 1995) in binding buffer comprised of 8 mM Na$_2$HPO$_4$, 0.87 mM KH$_2$PO$_4$, 136 mM NaCl, 112.6 mM KCl, 2 mM DTT and 2 mM MgCl$_2$(FIG. 1A). Incubation was done at 37° C. in an overhead incubator.

Cycles 1–7: After 60 min. beads were collected for 10 min. at 700 g.

Cycles 8–9: Incubation with immobilized GST was done for 30 min. as described above. Subsequently the beads were removed by centrifugation and the supernatant incubated with freshly immobilized GST for another 30 minutes.

Cycles 1–9: The supernatant from the preselection(s) was incubated with immobilized GST::rPrP$^c$23-231 (53 pMol) synthesized in the Baculovirus system (Weiss et al., 1995) as described above. After 60 minutes the beads were washed four times with binding buffer and the RNA eluted in the presence of 8 M urea in 100 mM sodium citrate pH 8.0 and 3 mM EDTA. The RNA was phenol (pH 5.0)/chloroform extracted and EtOH precipitated in the presence of 2 M NH$_4$-acetate (FIG. 1A).

Cycle 9 to 11: Selected RNA (40 pMol in the 9th; 4 pMol each in the 10th and 11th cycle) was 5' labeled and incubated with soluble GST::rPrP$^c$23-231 (Weiss et al., 1995; 140 pMol in the 9th cycle, 40 pMol in the 10th and 11th cycle) for 60 min. at 37° C. in binding buffer and analyzed by an gel retardation assay on an 0.7% native agarose gel (FIG. 1B) as described (Weiss et al., 1992). Following electrophoresis the RNA/GST::PrP$^c$23-231 complex was excised and extracted by employing an Qiaex extraction kit (Qiagen).

Cycles 1–11: 50% each of the extracted RNA was subjected to a reverse transcription reaction according to the Superscript reverse transcriptase kit (Gibco, BRL). 50% of the resulting cDNA was amplified by PCR according to Saiki et al., 1988 using the primers shown in FIG. 2B. 50% of the amplified cDNA was in vitro transcribed as described (Weiss et al., 1992).

Nitrocellulose binding assay: 4 pMol 5' labeled (Sambrook et al., 1989) RNA was incubated in the presence of 0 to 500 nM of protein in the presence of binding buffer for 60 min. at 37° C. The incubation mixture was filtered over a BA85 nitrocellulose membrane in a Millipore slot blot apparatus, the filter washed with 4 ml of incubation buffer, excised and measured by Cerenkov Counting.

Gel retardation assay: RNA and protein were incubated as described above and the reaction mixture loaded on a 0.7% native agarose gel as described (Weiss et al., 1992). Following electrophoresis, the gel was fixed by 5% TCA, dried and subjected to autoradiography.

RNA Pool M111.1: The RNA pool was prepared by in vitro transcription from a DNA pool (138 bases) as described (Famulok, 1994). In brief, M111.1 reveals a randomized sequence of 74, a base permutation of $4^{74}=3.56\times10^{44}$ molecules, a molecular weight of 36630 Dalton. Synthesis yielded 175 µg (4.76 nMol) RNA; that is $6\times10^{23}$ (Avogadro)$\times4.76\times10^{-9}=2.86\times10^{15}$ molecules. 36% of the synthesized ssDNA pool are extendible by PCR which resulted in a pool with approximately $1.03\times10^{15}$ different sequences and a complexity of $1.03\times10^{15}$, which is equivalent to one pool copy (i.e. each individual RNA molecule is represented one fold in the pool). In particular, the technical features of RNA pool M111.1 are the following:

Nucleotide sequence of fixed region 1
  5' CCGAATTCTAATACGACTCACTATAG-GAGCTCAGC CTTCACTGC (SEQ ID NO: 19)

Nucleotide sequence of fixed region 2
  5' GTGGATCCGACCGTGGTGCC (SEQ ID NO: 20)

randomized sequence=74 nucleotides base permutation $4^{74}=3.56\times10^{44}$;

MW=36630; 1 nM=36.63 µg;

175 µg (4.76 nMol) were synthesized; that is $6\times10^{23}\times 4.76\times10^{-9}=2.86\times10^{15}$ molecules 36% extendable pool complexity=$1.03\times10^{15}$ molecules=1 pool copy i.e. each individual RNA molecule is represented one fold in the pool.

A schematic view of RNA pool M111.1 is shown in FIG. 2. The nucleotide sequence 5'-CCGAATTCTAATACGACTCACTATA (nucleotides 1 to 25 of SEQ. ID NO: 19) of the fixed region 1 only belongs to the DNA pool since it is not transcribed.

After 9 rounds of selection 7.2% of the selected RNA bound to GST::rPrP$^c$23-231 immobilized on glutathione-sepharose 4B (Table 1 and FIG. 3).

The percentage of RNA-binding was determined as follows: Radioactivity associated with GST::rPrP$^c$ beads after removal of supernatant was set to 100%. Radioactivity retained after four washing steps represents the percentage of the RNA binding.

TABLE 1

RNA protein ratios and % binding of RNA to protein dependent on the selection cycle

| Cycle | RNA:GST (molar ratio) | RNA: GST::rPrP$^c$ (molar ratio) | % binding* (RNA to GST::rPrP$^c$) |
|---|---|---|---|
| 1 | 36:1 | 83:1 | 0 |
| 2 | 10:1 | 22:1 | 0 |
| 3 | 5:1 | 11:1 | 0 |
| 4 | 3.5:1 | 8:1 | 1 |
| 5 | 10:1 | 24:1 | 1.25 |
| 6 | 4.5:1 | 10:1 | 2.5 |
| 7 | 14:1 | 33:1 | 2.75 |
| 8 | 10:1/7:1 | 18:1 | 7.2 |
| 9 | 10:1/7:1 | 18:1 | 7.2 |

*The percentage of RNA binding was measured as described in the legend to Figure 3.

Figure 4:
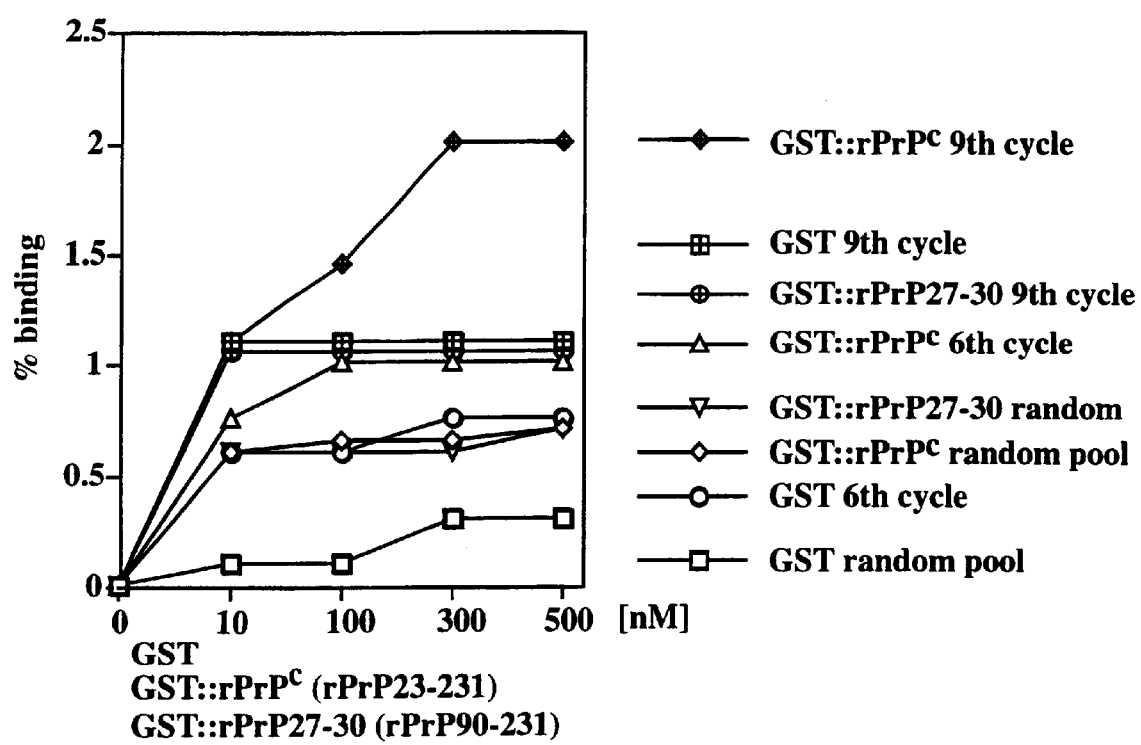
Figure 4:
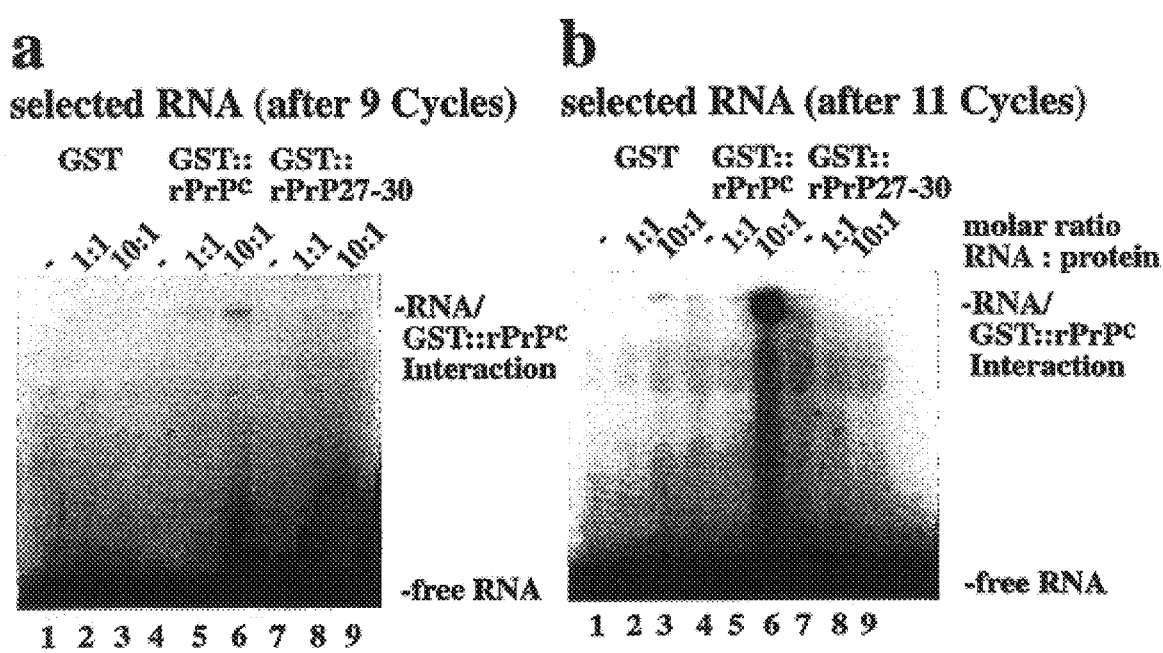

A binding assay employing soluble GST, GST::PrP$^c$23-231 and GST::rPrP27-30 revealed that 2% of the enriched RNA from cycle 9 bound to GST::PrP$^c$23-231 whereas only 1.1% bound to GST::rPrP27-30 and GST (FIG. 4 A). This result indicates that ~5% of the RNA bound to the matrix, i.e. glutathione-sepharose 4B. After 6 rounds of selection only 1% of the RNA bound to immobilized GST::PrP$^c$23-231 and 0.7% to GST (FIG. 4A).

A gel retardation assay with RNA isolated after 9 cycles of selection confirms that about 2% of the RNA bound to GST::PrP$^c$23-231 at a molar ratio of 10:1 (protein:RNA) (FIG. 4B, panel a, lane 6), whereas no binding occurs under identical conditions in the case of GST::rPrP27-30 (lane 9) and GST (lane 3).

To enrich RNA specifically binding to GST::PrP$^c$23-231 and to remove RNA molecules binding to the matrix. we excised the RNA/GST::PrP$^c$23-231 complex, extracted and amplified the RNA (FIG. 1B) and subjected it to two further gel retardation assays. As demonstrated in FIG. 4B after a total of 11 cycles (panel b) we isolated an RNA which bind specifically to GST::PrP$^c$23-231 at a 10 fold molar excess of protein over RNA (FIG. 4B, panel b, lane 6). No binding occurs in the presence of GST::rPrP27-30 (lane 9) and GST (lane 3). A more detailed binding analysis revealed that binding of RNA to GST::PrP$^c$23-231 occurs at a molar ratio (RNA:protein) between 1:1 and 5:1. These findings demonstrate the selection of an RNA which can distinguish between GST::PrP$^c$23-231 and GST::rPrP27-30.

These results demonstrate that it is possible to isolate an RNA aptamer (aptus=to fit) by in vitro selection which bind specifically to the cellular prion protein isoform PrP$^c$23-231 fused to GST. This RNA does not bind to the recombinant prion protein rPrP27-30 fused to GST and not to GST. Therefore a RNA was selected which can distinguish between PrP$^c$23-231 and rPrP27-30. Recombinant PrP27-30 share the same amino acid sequence compared to natural PrP27-30 present in Scrapie prion preparations (Prusiner et al., 1984) but reveals in contrast to the natural isoform proteinase K sensitivity.

The RNA aptamer able to distinguish between PrP$^c$23-231 and rPrP27-30 overcomes the problem that it is not possible to produce poly- and monoclonal PrP antibodies which recognize specifically only one PrP isoform (Groschup et al., 1984 and ref. therein) and provides a suitable tool for a reliable diagnostic of transmissible spongiform encephalopathy.

EXAMPLE 2

Determination of Sequences of the Identified RNA Molecules

In order to determine the sequences of RNA molecules identified after 11 cycles of amplification and selection, these RNA molecules were reversed transcribed into cDNA and amplified by PCR (Sambrook et al., 1989). The obtained cDNA was restricted with EcoRI and BamHI, subcloned into pGEM-3-Zf(-) and the sequence of 20 different cDNA clones pGEM-Ap 1 to 20 determined according to Sanger et al. (1977). Sequences of 14 RNA molecules identified are depicted in FIG. 5 (SEQ ID NO: 1 to 14). The obtained monoclonal RNAs revealed sequences which may contain G-quartet motifs. Three classes of G-quartet motifs (Table II; FIGS. 5A, B, C) could be identified with more than one monoclonal RNA. 30% of the sequenced DNA molecules encode for unique RNA molecules which may also contain G-quartets (FIG. 5D), 30% of the selected RNA aptamers did not contain any G-quartet motif (FIG. 5E).

TABLE II

Distribution of selected RNA aptamers.

|  | Motif I | Motif II | Motif III | G-quartet motif (unique) | no G-quartet motif |
|---|---|---|---|---|---|
| % of clones sequenced | 10 | 15 | 15 | 30 | 30 |

A detailed analysis of the 20 sequenced clones revealed that 70% of the clones contained four sets of three highly conserved consecutive guanosine residues, separated by single stranded regions between four and seven nucleotides long. These guanosine rich consensus motifs are flanked by two variable regions of predominantly Watson-Crick variation (see FIG. 6). The primary sequence of the molecules comprising the four sets of guanosine stretches strongly suggests that their secondary structure contains a three layered G-tetrad motif (see FIG. 6). In 40% of the selected RNAs three classes of aptamer motifs were identified based on their relationship within the three single stranded loop regions (see FIG. 6). While individual members of each identified class were identical in the putative G-tetrad and loop regions. they showed significant covariation in the Watson-Crick helix. Such G-tetrad motifs had already been identified in several other in-vitro selected nucleic acid molecules (see e.g. Bock et al., 1992; Wang et al., 1993; Macaya et al., 1993; Lauhon and Szostak, 1995; Huizenga and Szostak, 1995; Harada and Frankei, 1995) and appear to represent an important feature in nucleic acid molecules which bind to a ligand with high specificity. Furthermore, G-quartets have been suggested for telomeric DNA sequences in species such as Tetrahymena (Sundquist and Klug, 1989; Williamson et al., 1989; for review: Williamson, 1993). Guanine rich sequences which could form G-quartets were found in immunoglobulin switch regions, gene promoters and in chromosomal telomers which are thought to bring the four homologous chromatids together during meiosis and prevent the DNA from degradation (Sen and Gilbert, 1988). G-quartets have also been discussed to play a role in the dimerization process of retroviral genomic RNA (Weiss et al., 1993), a prerequisite for the generation of infectious virions. G-tetrads are held together by Hoogsteen base pairing through hydrogen bonds between nitrogens or oxygens and hydrogens (Sen and Gilbert, 1988). The RNA aptamers selected against the prion protein could contain three G-quartets stacked upon each other (FIG. 6) to form two eight-coordinate chelation cages. Alkali-metal ions such as potassium located within the axial channel are able to complex four oxygens of the upper and four oxygens of the lower G-quartet. Because of the very compact structure G-tetrads are very stable and unusual RNAse resistant.

EXAMPLE 3

Monoclonal RNA Aptamers Harboring G-quartet Motif I and II Bind Specifically to rPrP23-231 (rPrP$^c$) from Hamster and rPrP25-242 (rPrPC) from Calf Monoclonal RNA aptamers representing motif I (Ap1; FIGS. 6A, B) and II (Ap2; FIGS. 6C, D) interact specifically with rPrP23-231 (rPrP$^c$) from Syrian golden hamster (FIGS. 6A, C; lanes 2) and rPrP25-242 (rPrP$^c$) from cattle (FIGS. 6B, D; lanes 2) both fused to GST. Prion proteins from hamster and cattle reveal a sequence homology of 88%. Bovine PrP was synthesized in insect cells infected with a recombinant baculovirus containing bovine prn-p cDNA (Yoshimoto et al., 1992). Binding of the RNA aptamers to bovine PrP was investigated to prove whether the aptamers are suitable for the development of a BSE diagonostic tool. Both aptamers do not bind to the recombinant GST fused prion proteins rPrP90-231 (rPrP27-30) from hamster (FIGS. 6, A, C; lanes 3) and rPrP93-242 (rPrP27-30+1 octarepeat, aa 93-101) from cattle (FIGS. 6, B, D; lanes 3) demonstrating that the molecules distinguish between rPrP$^c$ and rPrP27-30 from both species. RNA aptamers of group III interact with rPrP$^c$ and show weak interaction with rPrP27-30. Some of the selected RNA aptamers lacking any G-quartet motif interact with GST (data not shown).

Furthermore, an aptamer was constructed consisting of 60 nucleotides on the basis of an aptamer comprising motif I as shown in FIG. 5, which, however, lacked the primer binding sites as well as 14 nucleotides of the randomized region. This 60-mer exactly corresponds to a part of one of the aptamers displaying the motif I as depicted in FIGS. 6A/B and displayed the same binding characteristics as the full-length aptamer. The sequence of this 60mer is depicted in SEQ ID NO: 18. This molecule was isolated by the following procedure: By using two appropriate primers, DNA containing the 60 nucleotides encoding the RNA motif I (FIG. 5A, #II; SEQ ID NO: 18) flanked by a T7 promoter was amplified by PCR (Sambrook et al., 1989) under the following conditions: 1 min 94° C. 1 min 52° C. and 2 min 72° C. for 25 cycles. The amplified cDNA product of 80 nucleotides was subjected to an in vitro transcription reaction (Sambrook et al., 1989) with T7 RNA polymerase leading to the RNA aptamer consisting of 60 nucleotides (motif I, FIGS. 6A, B). The RNA was gel purified before the use in gel retardation assays.

This 60 mer was also used for the determination of the equilibrium binding constants. For this purpose 4 pMol of 5' γ-$^{32}$P-ATP labelled and α-$^{32}$P-UTP labelled RNA aptamer motif I (SEQ ID NO: 18) was incubated in the presence of 0, 4, 20, 28, 40, 60, 80, 108 pMol of GST::rPrP23-231 for 60 min at 37° C. under assay conditions as described above. RNA/protein complexes have been analyzed by an gel retardation assay (Weiss et al., 1992). Gel was fixed by 5% TCA, dried and subjected to autoradiography for 12 hours. Intensities of the signals have been determined by phospho-imaging (ImageQuaNT™, Strom 860, Molecular Dynamics).

For the calculation of the equilibrium binding constant a bimolecular reaction between the RNA and the protein was assumed. The concentration [c] of the RNA/protein complex at equilibrium can be determined from the amount of radioactivity in the shifted position and the known specific activity of the RNA. For the calculation of the equilibrium binding constant ($K_D$) the following formula was used (Meisteremst et al., 1988; Schellenberger et al., 1989):

$$KD = \left[\frac{R_o}{[PR]_{eq}} - 1\right] \times [P]_{eq}$$

$R_o = R_{eq} + [RP]_{eq}$;
$P_{eq} = P_o - [RP]_{eq}$;
R=RNA aptamer motif I (60 mer)
P=GST::rPrP23-231 (GST::rPrP$^c$);

The following equilibrium binding constant ($K_D$) for the complex of the RNA aptamer (60 mer) and GST::rPrP23-231 (GST::␣PrP$^c$) was preliminary calculated as $K_D = 8 \times 10^{-7}$ M. Applying other models not basing on bimolecular binding reactions $K_D$ values $<8 \times 10^{-7}$ M are expected.

EXAMPLE 4

Mapping of the Hamster and Bovine PrP/aptamer Binding Site

Figure 7C:
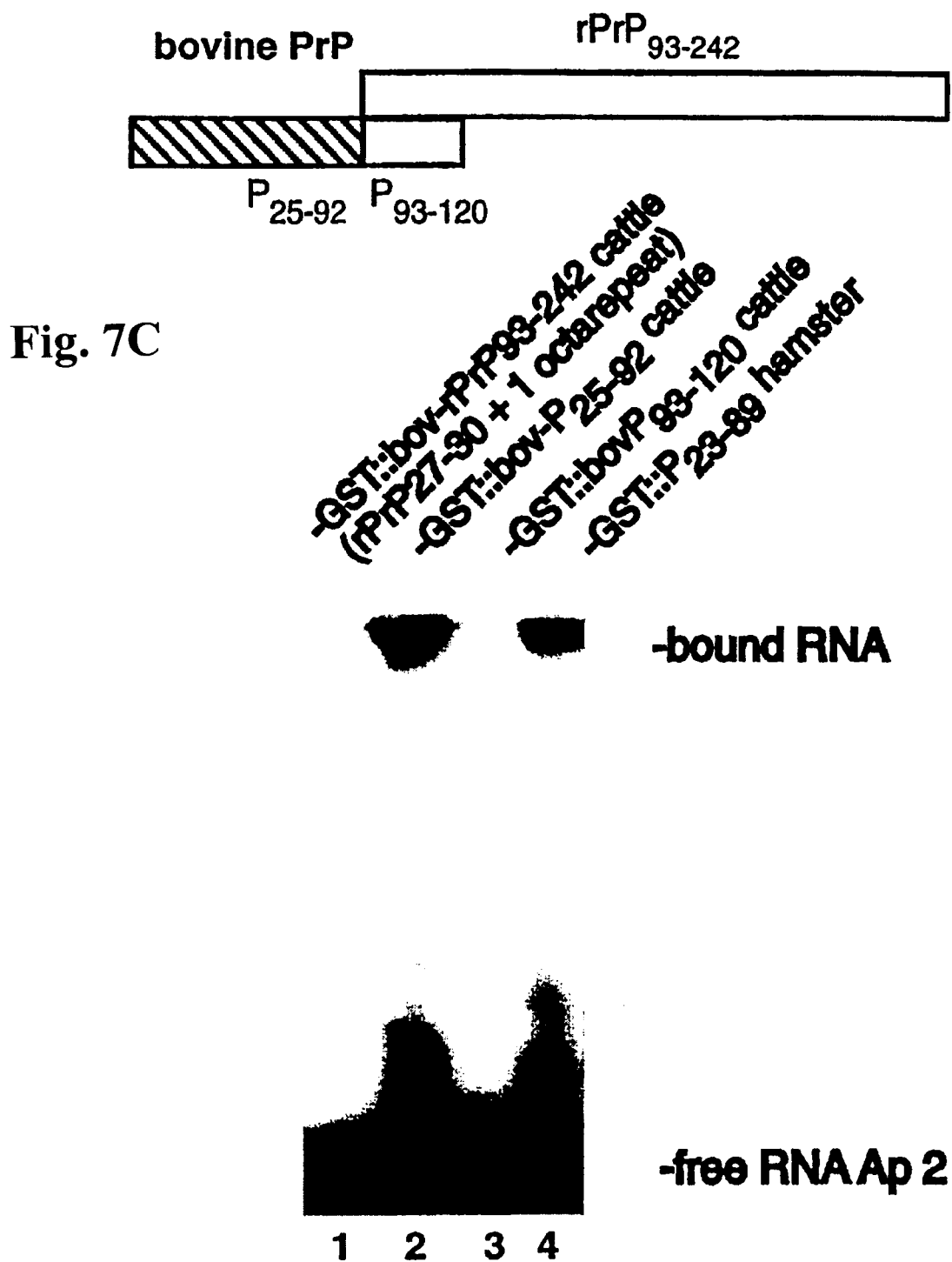

To map the interaction site of Syrian golden hamster PrPC to RNA aptamers 1 and 2, we employed a series of recombinant prion peptides (Weiss et al., 1995; FIGS. 7, A, B). Only peptide $P_{23-52}$ interact with RNA aptamers Ap1 and 2 (FIGS. 7, A, B), demonstrating that the amino terminal residues aa23 to aa52 of the Syrian golden hamster prion protein are sufficient for the recognition by both aptamers. Binding of the aptamers to rPrP27-30 failed because this molecule lacks the amino terminal 67 amino acid residues. Prion peptides $P_{25-92}$ and $P_{93-120}$ (FIG. 7C, lane 3) from bovine PrP have been synthesized to map the interaction site of bovine PrP$^c$ to RNA aptamer motif II. Only $P_{25-92}$ (FIG. 7C, lane 2) did bind to RNA aptamer motif 11 (Ap2) demonstrating that it is the amino terminus of the bovine prion protein which is recognized by the aptamer. Hamster peptide $P_{23-89}$ (FIG. 7C, lane 4) did also interact with aptamer Ap2 confirming the interaction of the amino terminus of the hamster prion protein with aptamer motif II.

Cited References

Aitken, R. Gilchrist. J. and Sinclair M. C. Vectors to facilitate the creation of translational fusions to the maltose-binding protein of *Escherichia coli*. Gene 144, (1994), 69–73.

Allen, P., Worland, S. and Gold, L.: Isolation of High-Affinity RNA Ligands to HIV-1 Integrase from a Random Pool. Virology 209 (1995), 327–336.

Basler, K., Oesch, B., Scott, M., Westaway, D., Wälchli, M., Groth, D. F., McKinley, M. P., Prusiner, S. B. and Weissmann, C.: Scrapie and cellular PrP isoforms are encoded by the same chromosomal gene. Cell 46 (1986), 417–428.

Bock, L. C. et al., Selection of single-stranded DNA molecules that bind and inhibit human thrombin. Nature 355 (1992), 564–566.

Brandner, S. et al., Normal host prion protein necessary for scrapie-induced neurotoxicity. Nature 379 (1996), 339–343.

Büeler, H. et al., Mice devoid of PrP are resistant to scrapie. Cell 73 (1993), 1339–1347.

Carr, D. W., Stofko-Hahn, R. E., Fraser, I. D. C., Bishop, S. M., Acott, T. S., Brennan, R. G. and Scott, J. D., Interaction of the regulatory subunit (RII) of cAMP-dependent protein kinase with RII-anchoring proteins occurs through an amphipathic helix binding motif. J. Biol. Chem. 266 (1991), 14188–14192.

Caughey, B. et al., N-terminal truncation of the Scrapie-associated form of PrP by lysosomal protease(s): Implications regarding the site of conversion of PrP to the protease-resistant state. J. Virol. 65 (1991), 6597–6603.

Collinge, J. et al., Prion protein is necessary for normal synaptic function. Nature 370 (1994), 295–297.

Edenhofer. F. et al., Prion protein PrP$^c$ interacts with molecular chaperones of the Hsp60 family. J. Virol. 70 (1996), 4724–4728.

Epstein, L., Cai. J.. Glaser, T., Jepeal, L. and Maas, R.: Identification of a Pax paired Domain recognition sequence and evidence for DNA-dependent conformational changes. J. Biol. Chem. 269 (1994), 8355–8361.

Famulok, M. and Szostak, J. W.: In vitro Selection of specific Ligand-binding Nucleic Acids. Angew. Chem. Int. Ed. Engl. 31 (1992), 979–988.

Famulok, M.: Molecular Recognition of Amino Acids by RNA-Aptamers: An L-Citrulline Binding Motif and its Evolution into an L-Arginine Binder. J.Am.Chem.Soc. 116(1994), 1698–1706.

Groschup, M. H., Langeveld, J. and Pfaff, E.: The major species specific epitope in prion proteins of ruminants. Arch. Virol. 136 (1994), 423–431.

Hampton, R. Y., Koning, A., Wright, R., and Rine, J., In vivo examination of membrane protein localization and degradation with green-fluorescent protein. Proc. Natl. Acad. Sci. USA 93 (1996), 828–833.

Harada, K. and Frankel, A. D., Identification of two novel arginine binding DNAs. EMBO J. 14 (1995), 5798–5811

Hope, J., Morton, L. J. D., Farquhar, C. F., Multhaup, G., Beyreuther, K. and Kimberlin, R. H., The major polypeptide of scrapie-associated fibrils (SAF) has the same size, charge distribution and N-terminal protein sequence as predicted for the normal brain protein (PrP). *EMBO J.* 5 (1986), 2591–2597.

Huizenga, D. E. and Szostak, J. W., A DNA aptamer that binds adenosine and ATP. Biochemistry 34 (1995), 656–665

Kawase, M., Mornoeda, M.. Young, N. S. and Kijagaya, S., Most of the VP1 unique region of B19 parvovirus is on the capsid surface. Virology 211 (1995), 359–366.

Kellings. K.. Meyer, N., Mirenda, C., Prusiner S. B., and Riesner, D.: Further analysis of nucleic acids in purified scrapie prion preparations by improved return refocusing gel electrophoresis. *J. Gen. Virol.* 73 (1992), 1025–1029.

Kim, J. S. and Raines, R. T., Ribonuclease S-peptide as a carrier in fusion proteins. Proteins Sci. 2 (1993), 348–356.

Kubik, M. F., Stephens, A. W., Schneider, D., Marlar, R. A. and Tasset, D.: High-affinity RNA ligands to human α-thrombin. Nucleic Acids Res. 22 (1994), 2619–2626.

Lansbury, P. T. Jr. and Caughey, B.: The chemistry of scrapie infection: implications of the ice 9' metaphor. *Chemistry & Biology* 2 (1995), 1–5.

Lauhon, C. T. and Szostak, J. W., RNA aptamers that bind flavin and nicotinamide redox cofactors. J. Am. Chem. Soc. 117 (1995), 1246–1257

Le-Grice, S. F. and Gruninger-Leitch, F., Rapid purification of homodimer and heterodimer HIV-1 reverse transcriptase by metal chelate affinity chromatography. Eur. J. Biochem. 187 (1990), 307–314.

Macaya, R. F. et al., Thrombin-binding DNA aptamer forms a unimolecular quadruplex structure in solution. Proc. Natl. Acad. Sci. USA 90 (1993), 3745–3749.

Meisterernst, M., Gander, I., Rogge, L. and Winnacker, E.-L.: A quantitative analysis of nuclear factor I/DNA interactions. Nucleic acids Res. 16 (1988), 4419–4435.

Oesch, B., Westaway, D., Wälchli, M., McKinley, M. P., Kent, S. B., Aebersold, R., Barry, R. A., Tempst, B., Teplow, D. B., Hood. L. E., Prusiner, S. B. and Weissmann, C.: A cellular gene encodes scrapie PrP27-30 protein. Cell 40 (1985), 735–746.

Pan, K.-M., Baldwin, M., Nguyen, J., Gasset, M., Serban, A., Groth, D., Mehlhorn. I., Huang, Z.. Fletterick. R. J., Cohen F. E. and Prusiner. S. B.: Conversion of α-helices into β-sheets features in the formation of the scrapie prion proteins. Proc. Natl. Acad. Sci. USA 90 (1993), 10962–10966.

Prusiner, S. B., McKinley, M. P., Groth, D. F., Bowman, K. A., Mack, N. I., Cochran, S. P. and Masiarz, F. R.: Scrapie agent contains a hydrophobic protein. Proc. Natl. Acad. Sci. USA. 78 (1981), 6675–6679.

Prusiner, S. B.: Novel proteinaceous infectious particles cause scrapie. Science 216 (1982), 136–144.

Prusiner, S. B., McKinley, M. P, Bowman, K. A., Bolton, D. C, Bendheim, P. E., Groth, D. F. and Glenner, G. G.: Scrapie prions aggregate to form amyloid-like birefringent rods. Cell 35 (1983), 349–358.

Prusiner, S. B., Groth, D. F., Bolton, D. C., Kent, S. B., and Hood, L. E.: Purification and structural studies of a major scrapie prion protein. Cell 38 (1984), 127–134.

Richards, F. M. and Wyckoff, H. W. in "The Enzymes" Vol IV (Boyer, P. D., Ed.) (1971), 647–806, Academic Press, New York.

Saiki, R. K., Gelfand, D. H., Stoffel,S., Scharf, S. J., Higuchi, R. Horn, G. T., Mullis, K. B. and Erlich, H. A.: Primer-directed enzymatic amplification of DNA with a thermostable DNA polymerase. Science 239 (1988), 487–491.

Sakaguchi, S. et al., Loss of cerebellar Purkinije cells in aged mice homozygous for disrupted PrP gene. Nature 380 (1996), 528–531.

Sakashita, E. and Sakamoto, H.: Characterization of RNA binding specificity of the Drosophila sex-lethal protein by in vitro ligand selection. Nucleic Acids. Res. 22 (1994), 4082–4086.

Sambrook J., Fritsch, E. F. and Maniatis, T.: Molecular Cloning. A Laboratory Manual. 2nd ed. Cold Spring Harbor Laboratory Press. Cold Spring Harbor, NY (1989).

Sanger, F. Nicklen. S. and Coulson. A. R. DNA sequencing with chain terminating inhibitors. Proc. Natl. Acad. Sci. USA 74 (1977), 5463–5467.

Schellenberger, A., Fischer, G., Hübner, G. and Ulbrich, R.: Enzymkatalyse. VEB Gustav Fischer Verlag, Jena (1989).

Sen, D. and Gilbert, W., Nature 334 (1988), 364–366

Stahl, N., Baldwin, M. A., Teplow, D. B., Hood, L., Gibson, B. W., Burlingame, A. L. and Prusiner, S. B.: Structural studies of the scrapie prion protein using mass spectrometry and amino acid sequencing. Biochemistry 32 (1993), 1991–2002.

Sundquist, W. I. and Klug, A., Telomeric DNA dimerizes by formation of guanine tetrades between hairpin-loops. Nature 342 (1989), 825–829

Tobler, I. et al., Altered carcadian activity rhythms and sleep in mice devoid of prion protein. Nature 380 (1996), 639–642

Tuerk, C. and Gold, L.: Systematic Evolution of Ligands by Exponential Enrichment: RNA Ligands to Bacteriophage T4 DNA polymerase. Science 249 (1990), 505–510.

Tuerk, C., MacDougal, S. and Gold, L.: RNA pseudoknots that inhibit human immunodeficiency virus type 1 reverse transcriptase. Proc. Natl. Acad. Sci. 89 (1992), 6988–6992.

Wang, K. Y. et al., The tertiary structure of a DNA aptamer which binds to and inhibits thrombin determines activity. Biochemistry 32 (1993), 11285–11292

Wang, L.-F., Yu. M., White, J. R. and Eaton, B. T., BTag: a novel six-residue epitope tag for surveillance and purification of recombinant proteins. Gene 169 (1996), 53–58.

Weiss, S. et al., The multimerization state of retroviral RNA is modulated by ammonium ions and effects HIV-1 full-length cDNA synthesis in vitro. Nucl. Acids Res. 21 (1993), 4879–4885.

Weiss, S., König, B., MCuller, H.-J., Seidel, H. and Goody, R. S.: Synthetic human tRNALys3 and natural bovine tRNALys3 interact with HIV-1 reverse transcriptase and serve as specific primers for retroviral cDNA synthesis. Gene 111 (1992), 183–197.

Weiss, S., Famulok, M., Edenhofer, F., Wang, Y.-H., Jones, I. M., Groschup, M., and Winnacker, E.-L.: Overexpression of Active Syrian Golden Hamster Prion Protein PrP$^c$ as a Glutathione S-Transferase Fusion in Heterologous Systems. J. Virol. 69 (1995), 4776–4783.

Weiss, S., Rieger, R., Edenhofer, F., Fisch, E. and Winnacker, E.-L.: Recombinant Prion Protein rPrP27-30 from Syrian Golden Hamster reveals Proteinase K Sensitivity, Biochem. Biophys. Res. Commun. 219 (1996), 173–179

Williamson, J. R. et al., Monovalent cation-induced structure of telomeric DNA: The G-quartet model. Cell 59 (1989), 871–880

Williamson, J. R. et al., G-quartets in biology: A reprise. Proc. Natl. Acad. Sci. USA 90 (1993), 3124

Yoshimoto, J., linuma, T., Ishiguro, N., Horiuchi, M., Imamura, M. and Shinagawa, M., Comparative sequence analysis and expression of bovine PrP gene in mouse L-929 cells. Virus genes 6 (1992), 343–356.

What is claimed is:

1. A nucleic acid molecule which comprises a nucleotide sequence selected from the group consisting of the sequences identified as SEQ ID NO:1 to SEQ ID NO:13 and SEQ ID NO:15 to SEQ ID NO:18.

2. The nucleic acid molecule according to claim 1 which comprises a nucleotide sequence selected from the group consisting of the sequences identified as SEQ ID NO:1 to SEQ ID NO:13.

3. The nucleic acid molecule according claim 1 which comprises the nucleotide sequence identified as SEQ ID NO:18.

4. A diagnostic composition comprising a nucleic acid molecule according to claim 1.

* * * * *

UNITED STATES PATENT AND TRADEMARK OFFICE
CERTIFICATE OF CORRECTION

PATENT NO. : 6,426,409 B1
DATED : July 30, 2002
INVENTOR(S) : Winnacker et al.

It is certified that error appears in the above-identified patent and that said Letters Patent is hereby corrected as shown below:

Title page,
Item [76], after "Weiss" replace "Blutenstrasse" with -- Blütenstrasse --

Column 1,
Line 28, after "minor", replace "extend" with -- extent --.
Line 30, replace "digestions" with -- digestion --.

Column 4,
Line 61, replace "Calmoduline" with -- Calmodulin --.

Column 5,
Line 31, replace "molecules" with -- molecule --.

Column 6,
Line 37, replace "the alive" with -- a live --.

Column 8,
Line 16, replace "labelled" with -- labeled --.
Line 62, after "by", replace "an" with -- a --.

Column 9,
Line 39, after "CTTCACTGC", add -- 3' --.
Line 41, after "5'GTGGATCCGACCGTGGTGCC", add -- 3' --.
Line 57, after "5'-CCGAATTCTAATACGACTCACTATA", add -- 3' --.

Column 10,
Line 50, after "which", replace "bind" with -- binds --.
Line 56, after "matrix", delete ".".
Line 56, replace "share" with -- shares --.

Column 12,
Line 7, replace "unusual" with -- unusually --.
Line 56, after "γ-$^{32}$P-ATP", replace "labelled" with -- labeled --; after "α-$^{32}$P-UTP", replace "labelled" with -- labeled --.

Column 14,
Line 33, after "5811", add -- . --.
Line 42, after "665", add -- . --.
Line 60, after "1257", add -- . --.

UNITED STATES PATENT AND TRADEMARK OFFICE
CERTIFICATE OF CORRECTION

PATENT NO. : 6,426,409 B1
DATED : July 30, 2002
INVENTOR(S) : Winnacker et al.

It is certified that error appears in the above-identified patent and that said Letters Patent is hereby corrected as shown below:

Column 15,
Line 21, after "11292", add -- . --.
Line 52, after "366", add -- . --.

Column 16,
Line 8, after "829", add -- . --.
Line 11, after "642", add -- . --.
Line 46, after "880", add -- . --.
Line 48, after "3124", add -- . --.

Column 18,
Line 43, after "179", add -- . --.

Signed and Sealed this

Twenty-sixth Day of November, 2002

Attest:

JAMES E. ROGAN
Attesting Officer *Director of the United States Patent and Trademark Office*

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 86 base pairs
        (B) TYPE: nucleic acid (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 1:

CACUGCAGCA AUUCGUUGUG CGGGAAUUUG AGGGACGAUG GGGAAGUGGG GACGAAUGAC     60

UCAUUGCCGC GGUAGGGUUA GGCACC     86

(2) INFORMATION FOR SEQ ID NO: 2:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 2:

CACUGCAGCA AUGCGUUGUG UGGGAAUUUG AGGGACGAUG GGGAAGUGGG GACGAAUGAC     60

UCAUUGCCGC GGUAGGGUUA GGCACC     86

(2) INFORMATION FOR SEQ ID NO: 3:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 3:

CACUGCUACC UUAGAGUAGG AGCGGGACGA GGGGUUGUUG GGACGUGGGU AUGAUCCAUA     60

CAUUAGGAAG CUGGUGAGCU GGCACC     86

(2) INFORMATION FOR SEQ ID NO: 4:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 4:

CACUGCUACC UUAGAGUAGG AGCGGGACGA GGGGUUGUUG GGACGUGGGU AUGAUCCAUA     60

CAUUAGGAAG CUGGUGAGCU GGCACC                                              86

(2) INFORMATION FOR SEQ ID NO: 5:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 5:

CACUGCUACC UUAGAGUAGG AGCGGGACGA GGGGUUGUUG GGACGUGGGU AUGAUCCAUA          60

CAUUAGGAAG CUGGUGAGCU GGCACC                                              86

(2) INFORMATION FOR SEQ ID NO: 6:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 6:

CACUGCGACA UGGGAAGAGG GAAGAGGGUU GUCGGGAGAU AAUGUCGCGA AACUAAGAAC          60

UCUAAGAGCU GCCCGGGCAC C                                                   81

(2) INFORMATION FOR SEQ ID NO: 7:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 7:

CACUGCGACA UGGGAGGAGG GAAGAGGGUU GUCGGGAGAU AAUGUCGCGA AACUAAGAAC          60

UCUAAGAGCU GCCCGUGGCA CC                                                  82

(2) INFORMATION FOR SEQ ID NO: 8:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: other nucleic acid (A) DESCRIPTION:   /desc = "RNA"

(iii) HYPOTHETICAL: YES (iv) ANTI-SENSE: NO (xi) SEQUENCE DESCRIPTION: SEQ ID NO: 8:

CACUGCGACA UGGGAAGAGG GAAGAGGGUU GUCGGGAGAU AAUGUCGCAA AGCUAAGAAC     60

UCUAAGAGCU GCCGCGUGGC ACC     83

(2) INFORMATION FOR SEQ ID NO: 9:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "RNA"

(iii) HYPOTHETICAL: YES (iv) ANTI-SENSE: NO (xi) SEQUENCE DESCRIPTION: SEQ ID NO: 9:

CACUGCUUGC UCGUUGCACU GUGAUAUGUG GGUUUAGGAU AGGGAGAAGG GAAGAGGGAA     60

GAAUAUCCGU CUGAACGAGG GCACC     85

(2) INFORMATION FOR SEQ ID NO: 10:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "RNA"

(iii) HYPOTHETICAL: YES (iv) ANTI-SENSE: NO (xi) SEQUENCE DESCRIPTION: SEQ ID NO: 10:

CACUGCUGCU AUUCAGUGGG UUGUGGGAGA AGGGUAGGGG GAUGAUGAAA GCAGCUCGUG     60

UGAUUUCUUU CUGAAGACCG GCACC     85

(2) INFORMATION FOR SEQ ID NO: 11:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "RNA"

(iii) HYPOTHETICAL: YES (iv) ANTI-SENSE: NO (xi) SEQUENCE DESCRIPTION: SEQ ID NO: 11:

CACUGCCGUC AUAUGGGCAC AUCUCAAAGU GGGAAUGUGG GGUGAUGGGA AGAGGGAUGA     60

UUAAGAUGGC CACAUAUUCG GCACC     85

(2) INFORMATION FOR SEQ ID NO: 12:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 12:

```
CACUGCGAGG AUGCGGGACG AGGGAACGUG GGAACGAGGG AUGAAUCCUU GUAGUGAGAU    60

AGCUUCCCCA ACAUGUCCAG GCACC                                         85
```

(2) INFORMATION FOR SEQ ID NO: 13:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 13:

```
CACUGCUCGC GUCAUUGGCA AGAGGGAAGU GGGAUGCGGG AAAGAUUGGG AACACCGCAC    60

CAAUAAUGUG AGUGUGAGGG GCACC                                         85
```

(2) INFORMATION FOR SEQ ID NO: 14:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 14:

```
CACUGCCUCG AAAACUGUGA AGAGUACGCU UUAACUGUGC UCCGUGUGGA UUGACCAUAG    60

ACCCGUCCCU GGACAGGCAC C                                             81
```

(2) INFORMATION FOR SEQ ID NO: 15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "RNA"

(iii) HYPOTHETICAL: YES (iv) ANTI-SENSE: NO (xi) SEQUENCE DESCRIPTION: SEQ ID NO: 15:

GGGAAUUUGA GGGACGAUGG GGAAGUGGG                                29

(2) INFORMATION FOR SEQ ID NO: 16:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "RNA"

(iii) HYPOTHETICAL: YES (iv) ANTI-SENSE: NO (xi) SEQUENCE DESCRIPTION: SEQ ID NO: 16:

GGGACGAGGG GUUGUUGGGA CGUGGG                                   26

(2) INFORMATION FOR SEQ ID NO: 17:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "RNA"

(iii) HYPOTHETICAL: YES (iv) ANTI-SENSE: NO (xi) SEQUENCE DESCRIPTION: SEQ ID NO: 17:

GGGAAGAGGG AAGAGGGUUG UCGGG                                    25

(2) INFORMATION FOR SEQ ID NO: 18:

(i) SEQUENCE CHARACTERISTICS:
           (A) LENGTH: 60 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "RNA"

(iii) HYPOTHETICAL: YES (iv) ANTI-SENSE: NO (xi) SEQUENCE DESCRIPTION: SEQ ID NO: 18:

GCAAUGCGUU GUGUGGGAAU UUGAGGGACG AUGGGGAAGU GGGGACGAAU GACUCAUUGC   60

(2) INFORMATION FOR SEQ ID NO: 19:

(i) SEQUENCE CHARACTERISTICS:
           (A) LENGTH: 44 base pairs
           (B) TYPE: nucleic acid
           (C) STRANDEDNESS: single
           (D) TOPOLOGY: linear (ii) MOLECULE TYPE: other nucleic acid
           (A) DESCRIPTION:   /desc = "oligodesoxynucleotide"

(iii) HYPOTHETICAL: YES (iv) ANTI-SENSE: NO (xi) SEQUENCE DESCRIPTION: SEQ ID NO: 19:

CCGAATTCTA ATACGACTCA CTATAGGAGC TCAGCCTTCA CTGC                    44

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligodesoxynucleotide"

(iii) HYPOTHETICAL: YES (iv) ANTI-SENSE: NO (xi) SEQUENCE DESCRIPTION: SEQ ID NO: 20:

GTGGATCCGA CCGTGGTGCC                                               20